(12) United States Patent
Padget et al.

(10) Patent No.: US 7,553,275 B2
(45) Date of Patent: Jun. 30, 2009

(54) MEDICAL DEVICE WITH ARTICULATING SHAFT

(75) Inventors: Martin Padget, Valencia, CA (US); David Skinlo, Ventura, CA (US); Thomas Weisel, Ventura, CA (US); Longo Chu, Newhall, CA (US)

(73) Assignee: Surgical Solutions LLC, Valencia, CA (US)

( * ) Notice: Subject to any disclaimer, the term of this patent is extended or adjusted under 35 U.S.C. 154(b) by 530 days.

(21) Appl. No.: 11/211,834

(22) Filed: Aug. 25, 2005

(65) Prior Publication Data

US 2006/0074407 A1 Apr. 6, 2006

Related U.S. Application Data

(60) Provisional application No. 60/606,245, filed on Aug. 31, 2004, provisional application No. 60/646,966, filed on Jan. 24, 2005, provisional application No. 60/676,456, filed on Apr. 28, 2005.

(51) Int. Cl.
*A61B 1/00* (2006.01)

(52) U.S. Cl. .................. 600/142; 600/139; 600/141; 606/1

(58) Field of Classification Search .............. 606/1; 600/137, 139, 121, 141–144, 149, 146, 101, 600/128, 130; 128/898
See application file for complete search history.

(56) References Cited

U.S. PATENT DOCUMENTS

| | | | | |
|---|---|---|---|---|
| 2,028,635 A | 1/1936 | Wappler | ................. | 174/89 |
| 3,190,286 A * | 6/1965 | Stokes | ................. | 600/141 |
| 3,314,431 A | 4/1967 | Smith, Jr. | ................. | 128/351 |
| 3,470,876 A | 10/1969 | Barchilon | ................. | 128/348 |
| 3,605,725 A | 9/1971 | Bentor | | |
| 3,788,303 A | 1/1974 | Hall | ................. | 128/4 |
| 4,407,273 A * | 10/1983 | Ouchi | ................. | 600/107 |
| 4,483,562 A | 11/1984 | Schoolman | ................. | 294/19 |
| 4,662,371 A | 5/1987 | Whipple | ................. | 128/312 |
| 4,672,964 A | 6/1987 | Dee | ................. | 128/305 |
| 4,686,963 A * | 8/1987 | Cohen et al. | ................. | 600/141 |
| 4,763,669 A | 8/1988 | Jaeger | ................. | 128/751 |
| 4,790,294 A | 12/1988 | Allred, III et al. | ................. | 600/141 |
| 4,790,624 A * | 12/1988 | Van Hoye et al. | ................. | 385/118 |
| 4,796,607 A * | 1/1989 | Allred et al. | ................. | 600/141 |
| 4,834,069 A | 5/1989 | Umeda | ................. | 128/4 |
| 4,880,015 A | 11/1989 | Nierman | ................. | 128/751 |

(Continued)

FOREIGN PATENT DOCUMENTS

DE 3920706 6/1989

(Continued)

*Primary Examiner*—John P Leubecker
*Assistant Examiner*—Victoria W Chen
(74) *Attorney, Agent, or Firm*—Myers Andras Sherman LLP; Joseph C. Andras

(57) ABSTRACT

A medical device includes an articulating shaft with a pair of slat assemblies. By moving an articulator, the slat assemblies are configured to concurrently push while the other pulls in order to bend the articulating shaft. The articulating shaft includes a series of alternating pins and pivot members. Each pin defines an aperture that collectively forms a passageway for receiving an actuator or a tube. The pair of slat assemblies extend generally parallel to each other on opposite sides of the pins. A method for articulating a shaft of a medical device is also provided.

24 Claims, 8 Drawing Sheets

U.S. PATENT DOCUMENTS

| | | | | |
|---|---|---|---|---|
| 4,934,340 A | 6/1990 | Ebling et al. | | 128/6 |
| 4,945,920 A | 8/1990 | Clossick | | 128/751 |
| 5,025,804 A | 6/1991 | Kondo | | 128/4 |
| 5,042,707 A | 8/1991 | Taheri | | 606/179 |
| 5,067,957 A | 11/1991 | Jervis | | 606/108 |
| 5,143,475 A | 9/1992 | Chikama | | 403/291 |
| 5,171,314 A | 12/1992 | Dulebohn | | 606/113 |
| 5,178,129 A | 1/1993 | Chikama | | 128/4 |
| 5,195,968 A | 3/1993 | Lundquist | | 604/95 |
| 5,201,741 A | 4/1993 | Dulebohn | | 606/113 |
| 5,209,747 A | 5/1993 | Knoepfler | | 606/16 |
| 5,254,130 A | 10/1993 | Poncet | | 606/206 |
| 5,284,128 A | 2/1994 | Hart | | 128/4 |
| 5,289,963 A | 3/1994 | McGarry | | 227/175 |
| 5,300,087 A | 4/1994 | Knoepfler | | 606/52 |
| 5,308,324 A | 5/1994 | Hammerslag | | 604/95 |
| 5,318,528 A | 6/1994 | Heaven | | 604/95 |
| 5,330,502 A | 7/1994 | Hassler | | 606/205 |
| 5,352,237 A | 10/1994 | Rodak | | 606/206 |
| 5,403,342 A | 4/1995 | Tovey | | 606/205 |
| 5,405,344 A | 4/1995 | Williamson | | 606/1 |
| 5,417,203 A | 5/1995 | Tovey | | 128/4 |
| 5,431,323 A | 7/1995 | Smith | | 227/177 |
| 5,450,842 A | 9/1995 | Tovey | | 606/20 |
| 5,454,827 A | 10/1995 | Aust | | 606/170 |
| 5,468,250 A | 11/1995 | Paraschac | | 606/205 |
| 5,478,003 A | 12/1995 | Green | | 227/176 |
| 5,480,382 A | 1/1996 | Hammerslag | | 640/95 |
| 5,484,095 A | 1/1996 | Green | | 227/181 |
| 5,487,757 A | 1/1996 | Truckai | | 604/122 |
| 5,497,933 A | 3/1996 | DeFonzo | | 227/175 |
| 5,501,654 A | 3/1996 | Failla | | 606/170 |
| 5,507,773 A | 4/1996 | Huitema | | 606/207 |
| 5,520,678 A | 5/1996 | Heckele | | 606/207 |
| 5,531,686 A | 7/1996 | Lundquist | | 604/95 |
| 5,535,754 A | 7/1996 | Doherty | | 128/751 |
| 5,540,706 A | 7/1996 | Aust | | 606/170 |
| 5,549,637 A | 8/1996 | Crainich | | 606/207 |
| 5,562,682 A | 10/1996 | Oberlin | | 606/139 |
| 5,569,270 A | 10/1996 | Weng | | 606/144 |
| 5,582,617 A | 12/1996 | Klieman | | 606/170 |
| 5,588,964 A | 12/1996 | Imran et al. | | 604/95 |
| 5,609,601 A | 3/1997 | Kolesa | | 606/170 |
| 5,618,294 A | 4/1997 | Aust | | 606/170 |
| 5,620,415 A | 4/1997 | Lucey | | 604/22 |
| 5,620,447 A | 4/1997 | Smith | | 606/79 |
| 5,632,432 A | 5/1997 | Schulze | | 227/176.1 |
| 5,643,294 A | 7/1997 | Tovey | | 606/148 |
| 5,645,075 A | 7/1997 | Palmer | | 128/749 |
| 5,649,955 A | 7/1997 | Hashimoto | | 606/205 |
| 5,662,662 A | 9/1997 | Bishop | | 606/143 |
| 5,669,544 A | 9/1997 | Schulze | | 227/176.1 |
| 5,669,926 A | 9/1997 | Aust | | 606/170 |
| 5,673,840 A | 10/1997 | Schulze | | 227/175.1 |
| 5,673,841 A | 10/1997 | Schulze | | 227/175.1 |
| 5,680,982 A | 10/1997 | Schulze | | 227/175.1 |
| 5,692,668 A | 12/1997 | Schulze | | 227/175.1 |
| 5,702,408 A | 12/1997 | Wales | | 606/139 |
| 5,704,534 A | 1/1998 | Huitema | | 227/175.1 |
| 5,713,505 A | 2/1998 | Huitema | | 227/179.1 |
| 5,725,536 A | 3/1998 | Oberlin | | 606/170 |
| 5,752,973 A | 5/1998 | Kieturakis | | 606/207 |
| 5,766,196 A | 6/1998 | Griffiths | | 606/170 |
| 5,766,205 A | 6/1998 | Zvenyatsky | | 606/206 |
| 5,782,828 A | 7/1998 | Chen et al. | | 606/42 |
| 5,782,859 A | 7/1998 | Nicholas | | 606/205 |
| 5,797,537 A | 8/1998 | Oberlin | | 227/176.1 |
| 5,810,716 A | 9/1998 | Mukherjee | | 600/146 |
| 5,820,009 A | 10/1998 | Melling | | 227/176.1 |
| 5,823,066 A | 10/1998 | Huitema | | 74/527 |
| 5,833,692 A | 11/1998 | Cesarini | | 606/79 |
| 5,840,043 A | 11/1998 | Palmer | | 600/564 |
| 5,851,212 A | 12/1998 | Zirps | | 606/167 |
| 5,857,964 A | 1/1999 | Konstorum | | 600/139 |
| 5,860,995 A | 1/1999 | Berkelaar | | 606/174 |
| 5,885,288 A | 3/1999 | Aust | | 606/170 |
| 5,899,914 A | 5/1999 | Zirps | | 606/170 |
| 5,919,199 A | 7/1999 | Mers Kelly et al. | | 606/139 |
| 5,921,956 A * | 7/1999 | Grinberg et al. | | 604/95.01 |
| 5,938,678 A | 8/1999 | Zirps | | 606/170 |
| 5,967,997 A | 10/1999 | Turturro | | 600/567 |
| 6,033,378 A | 3/2000 | Lundquist | | 604/95 |
| 6,048,307 A * | 4/2000 | Grundl et al. | | 600/146 |
| 6,048,339 A | 4/2000 | Zirps | | 604/525 |
| 6,051,010 A | 4/2000 | DiMatteo | | 606/169 |
| 6,053,907 A | 4/2000 | Zirps | | 606/169 |
| 6,063,098 A | 5/2000 | Houser | | 606/169 |
| 6,068,648 A | 5/2000 | Cole | | 606/232 |
| 6,077,287 A | 6/2000 | Taylor | | 606/170 |
| 6,312,438 B1 * | 11/2001 | Adams | | 606/159 |
| 6,319,195 B1 | 11/2001 | Nakaichi | | 600/120 |
| 6,464,703 B2 | 10/2002 | Bartel | | 606/51 |
| 6,491,626 B1 | 12/2002 | Matsuura | | 606/141 |
| 6,554,844 B2 | 4/2003 | Lee | | 606/130 |
| 6,569,105 B1 | 5/2003 | Korenbach | | 600/562 |
| 6,585,718 B2 | 7/2003 | Hayzelden | | 600/523 |
| 6,607,496 B1 | 8/2003 | Poor | | 600/585 |
| RE38,335 E | 11/2003 | Aust et al. | | 606/170 |
| 6,645,218 B1 | 11/2003 | Cassidy | | 606/170 |
| 6,666,854 B1 | 12/2003 | Lange | | 606/1 |
| 6,702,780 B1 | 3/2004 | Gilboa | | 604/528 |
| 6,716,207 B2 | 4/2004 | Farnholtz | | 604/523 |
| 6,743,239 B1 | 6/2004 | Kuehn | | 606/170 |
| 6,743,240 B2 | 6/2004 | Smith | | 606/142 |
| 6,802,840 B2 | 10/2004 | Chin | | 606/15 |
| 6,824,548 B2 | 11/2004 | Smith | | 606/142 |
| 6,863,668 B2 | 3/2005 | Gillespie | | 606/1 |
| 6,869,414 B2 | 3/2005 | Simpson | | 604/528 |
| 6,877,647 B2 | 4/2005 | Green | | 227/176.1 |
| 6,921,408 B2 | 7/2005 | Sauer | | 606/145 |
| 2003/0018323 A1* | 1/2003 | Wallace et al. | | 606/1 |
| 2003/0032970 A1 | 2/2003 | Hiltebrandt | | 606/180 |
| 2003/0083550 A1* | 5/2003 | Miyagi | | 600/141 |
| 2003/0171650 A1* | 9/2003 | Tartaglia et al. | | 600/114 |
| 2004/0122449 A1 | 6/2004 | Modesitt | | 606/144 |
| 2004/0167547 A1 | 8/2004 | Beane | | |
| 2004/0236316 A1 | 11/2004 | Danitz | | 606/1 |
| 2005/0006430 A1 | 1/2005 | Wales | | 227/178.1 |

FOREIGN PATENT DOCUMENTS

| | | |
|---|---|---|
| DE | 3920706 A1 | 6/1989 |
| DE | 4136861 | 11/1991 |
| DE | 4136861 A1 | 11/1991 |
| DE | 4204051 | 2/1992 |
| DE | 4204051 A1 | 2/1992 |
| EP | 0301288 | 7/1988 |
| EP | 0301288 | 2/1989 |
| FR | 2662778 | 5/1990 |
| FR | 2662778 | 12/1991 |
| WO | WO 93/00048 | 6/1991 |
| WO | WO9300048 | 1/1993 |
| WO | WO 93/04634 | 3/1993 |
| WO | WO9304634 | 3/1993 |
| WO | WO 93/20760 | 4/1993 |
| WO | WO9320760 | 10/1993 |

* cited by examiner

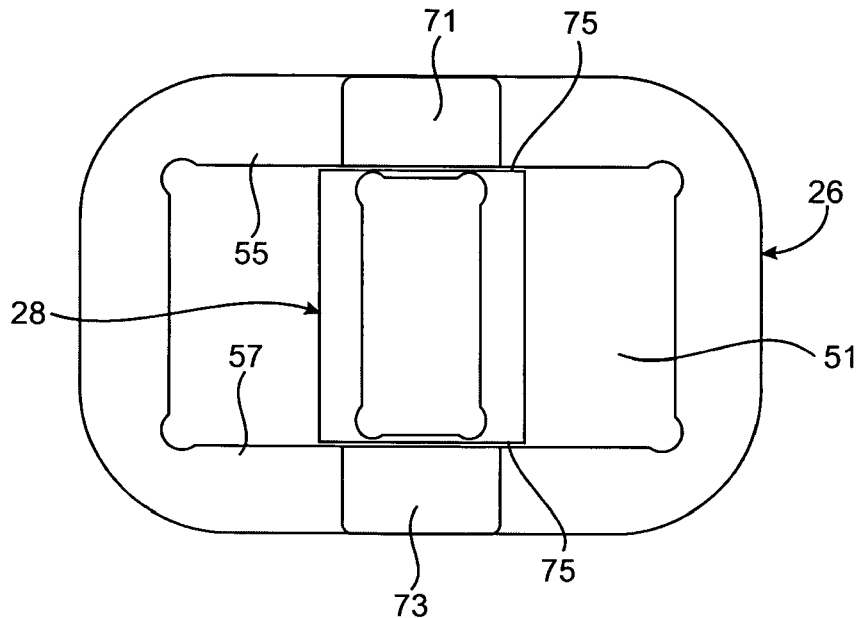
FIG. 6
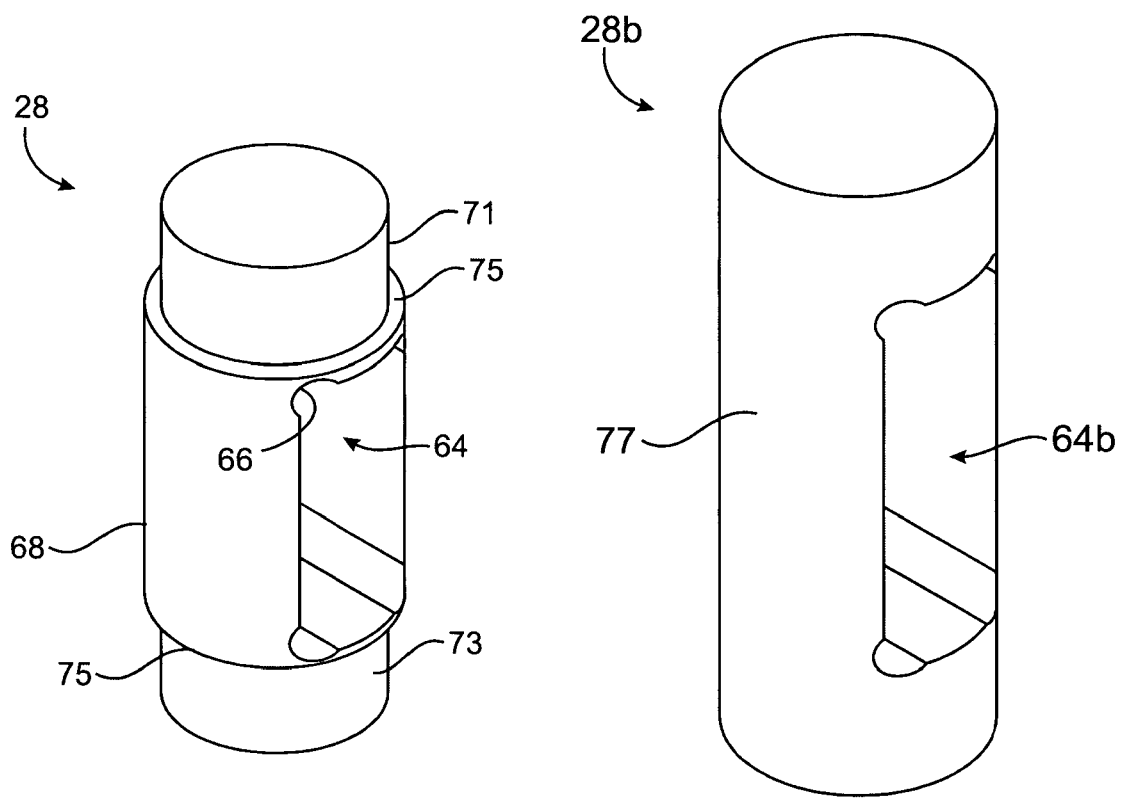
FIG. 5
FIG. 7

MEDICAL DEVICE WITH ARTICULATING SHAFT

RELATED APPLICATIONS

This application relates to, claims priority from, and incorporates herein by reference, as if fully set forth, the following:

1) U.S. Provisional Patent Application Ser. No. 60/606,245 filed on Aug. 31, 2004 and entitled "METHOD OF CREATING A FLEXIBLE SHAFT";

2) U.S. Provisional Patent Application Ser. No. 60/646,966 filed on Jan. 24, 2005 and entitled "METHOD OF CREATING A FLEXIBLE SHAFT"; and 3) U.S. Provisional Patent Application Ser. No. 60/676,456 filed on Apr. 28, 2005 and entitled "METHOD OF CREATING A FLEXIBLE SHAFT, PART C".

BACKGROUND OF THE INVENTION

1. Field of the Invention

The invention relates generally to surgical devices and methods, and more particularly to shafts.

2. Description of Prior Art and Related Information

In various types of surgical procedures, particularly in endoscopy, a need exists for articulating, or bendable shafts. Such shafts are preferable, and often times necessary, for circumnavigating particular areas in the human body in order to reach a specific destination therein. Articulating shafts in the prior art include complex mechanisms that are expensive to manufacture and difficult to assemble. These complexities have derived, at least in part, from the need to provide tension in order to cause the shaft to bend.

Such shafts in the prior art include flexible portions which can bend in only one direction through the use of various types of tensioning mechanisms. Since the pathway to a particular desired location in a human body is often circuitous in more intricate surgical procedures, bending a shaft in only one direction can be very limiting. To overcome this deficiency, mechanisms to rotate a one-way bending shaft have been employed. Of course, having to manipulate a knob to rotate a shaft and then having to pull a tension mechanism to bend a shaft increases the complexity of a surgical procedure.

Prior art articulating shafts also include those that bend in opposite directions. Nonetheless, the bending of such shafts is accomplished by tension which means that at least two tensioning mechanisms are provided: one to cause the bend in a first direction, and the other to cause the bend in an opposite direction. Use of these types of shafts requires the technician to select the appropriate tensioning mechanism.

Articulating shafts in the prior art are also highly complex. These complexities have derived from the requirement of bending a distal portion of a shaft with a mechanism located at a proximal end of a medical device. Such complexities relate to both the manufacturing and operation of these devices. Prior art articulating shafts also lack rigidity. This is due at least in part to the fact that tensioning mechanisms in the prior art do not provide sufficient rigidity. Under standard use, prior art shafts are often unable to maintain a sufficient articulated form or shape.

No simple structure has been devised to accomplish this.

SUMMARY OF THE INVENTION

In accordance with the present invention, structures and associated methods are disclosed which address these needs and overcome the deficiencies of the prior art.

In one aspect, a medical device comprises a bendable portion, or articulating shaft. The bendable portion includes a plurality of independent pivot members and pins in an alternating configuration. Each pivot member defines an opening while each pin defines a pin aperture. A first slat assembly and second slat assembly extend through the bendable portion. Each of the first slat assembly and the second slat assembly is configured to push when the other of the first slat assembly and the second slat assembly pulls so as to cause the bending portion to bend.

The openings collectively define an outer passageway while the pin apertures collectively define an inner passageway. The first slat assembly extends through the outer passageway alongside a first side of the pins while the second slat assembly extends through the outer passageway alongside a second side of the pins opposite the first side of the pins. The inner passageway provides a path for an actuator, a flexible tube, electrical wiring and/or light transmitting media, such as optical fibers, to extend through the bendable portion. The actuator may be formed with a variety of cross-sectional shapes, such as a rectangle, square, circle, etc.

An articulator is coupled to the first slat assembly and the second slat assembly such that operation of the articulator causes one of the first and second slat assemblies to push and the other of the first and second slat assemblies to pull simultaneously. In a preferred embodiment, movement of the articulator in one direction causes the bendable portion to bend in an opposite direction away from the direction of movement of the articulator. Alternatively, intermediate mechanisms may be coupled to the slat assemblies and the articulator to reverse this motion such that movement of the articulator in one direction causes the bendable portion to bend toward the same direction. Each pivot member defines a vertical axis. The device may comprise means for preventing each pin from moving vertically with respect to an adjacent pivot member. Each pivot member preferably has a laterally tapered thickness.

The first slat assembly comprises at least one slat and preferably a first plurality of layered slats. The second slat assembly comprises at least one slat and preferably a second plurality of layered slats. The device further comprises a rigid shaft portion coupled proximally to the bendable portion. The bendable portion may comprise a preconfigured and permanent curve that is disposed, or bent, in a direction generally perpendicular to the range of motion of the bendable portion. For example, the preconfigured curve may be bent upward or downward with respect to the rigid shaft portion.

In another aspect, a medical device comprises a bendable portion including a series of pivot members and pins in an alternating configuration. A first slat assembly is coupled to the bendable portion. A second slat assembly coupled to the bendable portion. Each of the first slat assembly and the second slat assembly is configured to push when the other of the first slat assembly and the second slat assembly pulls so as to cause the bendable portion to bend.

In an alternative embodiment, each pivot member comprises a pair of arms extending in opposite directions so as to form a first plurality of arms disposed along a first side of the pivot members and a second plurality of tabs disposed along a second opposite side of the pivot members. The first slat assembly comprises a first slat groove for receiving the first plurality of tabs. The second slat assembly comprises a second slat groove for receiving the second plurality of tabs.

In a further aspect, a method is provided for articulating a shaft of a medical device. The method comprises providing pivot members each having a single opening, extending a first slat assembly through the single opening of each pivot member, extending a second slat assembly through the single opening of each pivot member, pushing one of the first and second slat assemblies while concurrently pulling the other of the first and second slat assemblies to cause the pivot members to collectively form a bend.

The method further comprises providing pins each having a single pin aperture, and disposing the pins adjacent to the pivot members in an alternating configuration. The step of pushing one of the first and second slat assemblies while concurrently pulling the other of the first and second slat assemblies comprises moving an articulator. The step of moving the articulator comprises moving the articulator to a left direction to cause the pivot members to collectively form a bend in a first direction, and moving the articulator to the right direction to cause the pivot members to collectively form a bend in a second direction.

The method further comprises actuating an end operating, or tool, assembly coupled distally to the articulating shaft.

In summary, a medical device includes an articulating shaft with a pair of slat assemblies. By moving an articulator, the slat assemblies are configured to concurrently push while the other pulls in order to bend the articulating shaft. The articulating shaft includes a series of alternating pins and pivot members. Each pin defines an aperture that collectively forms a passageway for receiving an actuator or a tube. The pair of slat assemblies extend generally parallel to each other on opposite sides of the pins. A method for articulating a shaft of a medical device is also provided.

The invention, now having been briefly summarized, may be better visualized by turning to the following drawings wherein like elements are referenced by like numerals.

BRIEF DESCRIPTION OF THE DRAWINGS

FIG. 5 is a perspective view of a preferred pin;

FIG. 6 is front elevation view of a pivot member and the pin;

FIG. 7 is a perspective view an alternate pin;

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

Figure 1:
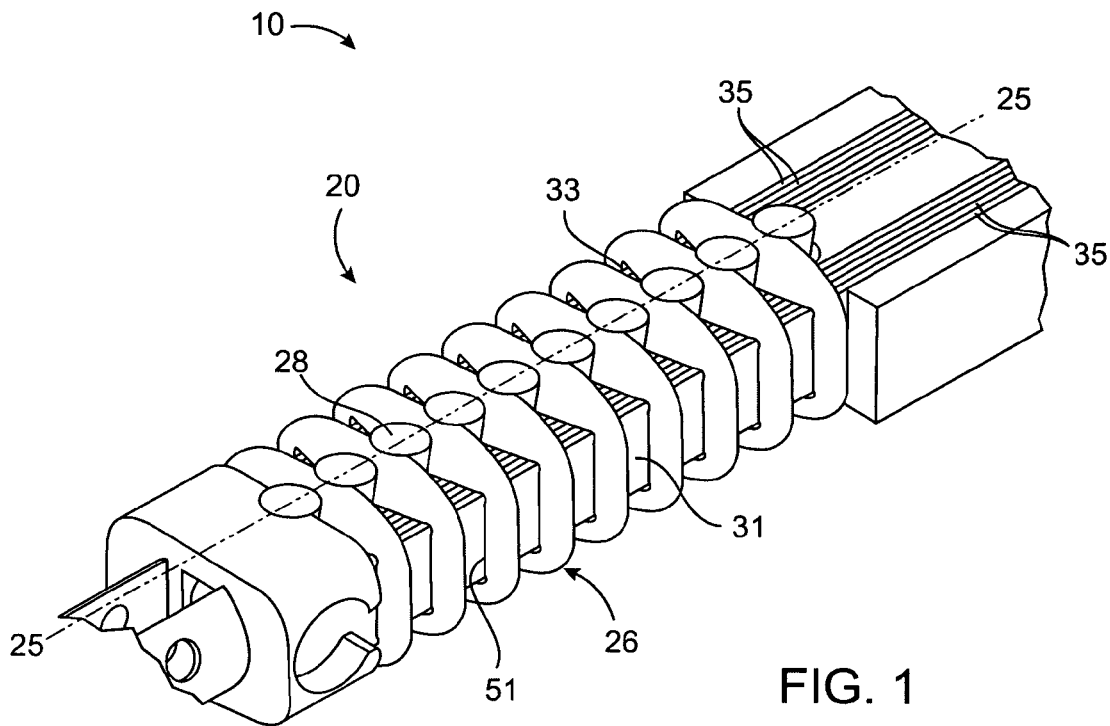
FIG. 1 is a perspective view of a first preferred embodiment of an articulating shaft according to the invention.
Figure 2:
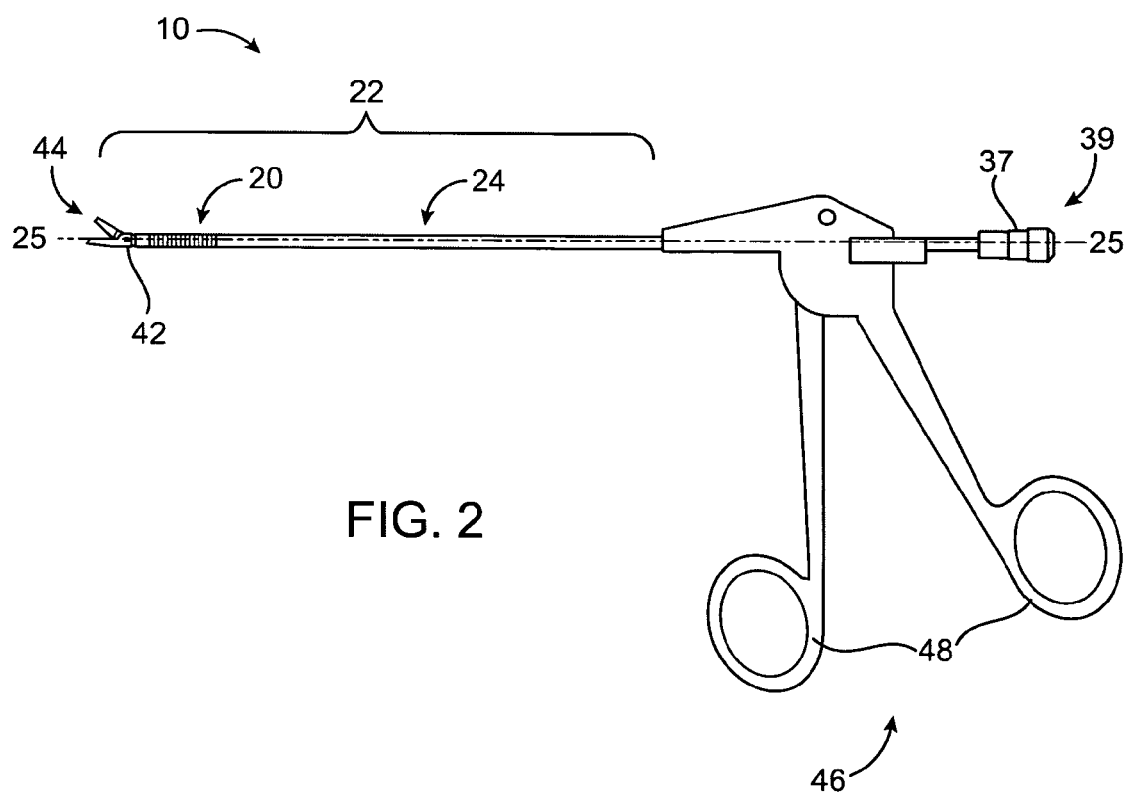
FIG. 2 is a side elevation view of a preferred medical device according to the invention.

A first preferred embodiment of a medical device is illustrated in FIGS. 1 and 2 and designated generally by the reference numeral 10. The medical device, or instrument, 10 is particularly configured for intricate surgical procedures where a direct, straight path to a desired destination is unavailable. In particular, endoscopic surgeries typically require circumnavigation around particular areas within the human body in order to reach a desired location for treatment.

The device 10 includes an articulating shaft, or bendable portion, 20 of particular interest to the invention. The articulating shaft 20 is formed as a distal portion of an overall shaft 22 that also includes a proximal rigid shaft portion 24. The overall shaft 22 defines a longitudinal axis 25. In the first preferred embodiment, the articulating shaft 20 comprises a plurality of independent pivot members 26 and pins 28 disposed in an alternating configuration. Thus, each pin 28 abuts an adjacent, but separate pivot member 26 in a rotatable, or pivotable, relationship as described in further detail below.

The device 10 comprises a first slat assembly 31 and a second slat assembly 33. Each slat assembly 31, 33 comprises at least one flat, elongate slat 35 that is generally elongate, flat and thin. The slats 35 are preferably composed of a super elastic material such as Nitinol. In the preferred embodiment, each slat assembly 31, 33 comprises a plurality of slats 35 disposed, or layered, side-by-side. Alternatively, the slat assemblies 31, 33 may include layers of other material, such as TEFLON®, disposed in between the slats 35. The slats are preferably disposed in a vertical orientation with respect to the shaft 20 so as to restrict the pivot members 26 from vertical movement. Except for the bending accomplished by the axial movement of the slat assemblies 31, 33 as described below, the slat assemblies 31, 33 also restrict individual sideways movement of any particular pivot member 26 and pin 28. In FIG. 2, the slat assemblies 31, 33 are ultimately coupled to an articulating mechanism, or articulator, 37 provided at a proximal end 39 of the device 10.

In FIG. 2, an operating mechanism 42 is coupled to the articulating shaft 20 generally at a distal end 44 of the device 10. In the illustrated embodiment shown in FIG. 2, the operating mechanism 42 is shown as forceps with a pair of jaws. It is to be expressly understood, however, that the device 10 may comprise a variety of operating mechanisms and tools at the distal end 44. As examples and not by way of limitation, the device 10 may comprise graspers, clips, suturing mechanisms, cutters, shavers, retractors, water jet cutters, RF ablation devices, imaging and/or light transmitting fibers (e.g., lasers, optical fibers, etc.) and a host of other mechanisms coupled to a distal end of the articulating shaft 20 according to the invention. Where actuation of a particular operating mechanism is necessary, the device 10 may comprise a proximal handle assembly 46 which includes a pair of handles 48, one of which is coupled to an actuator (hidden) extending through the overall shaft 22.

Figure 3:
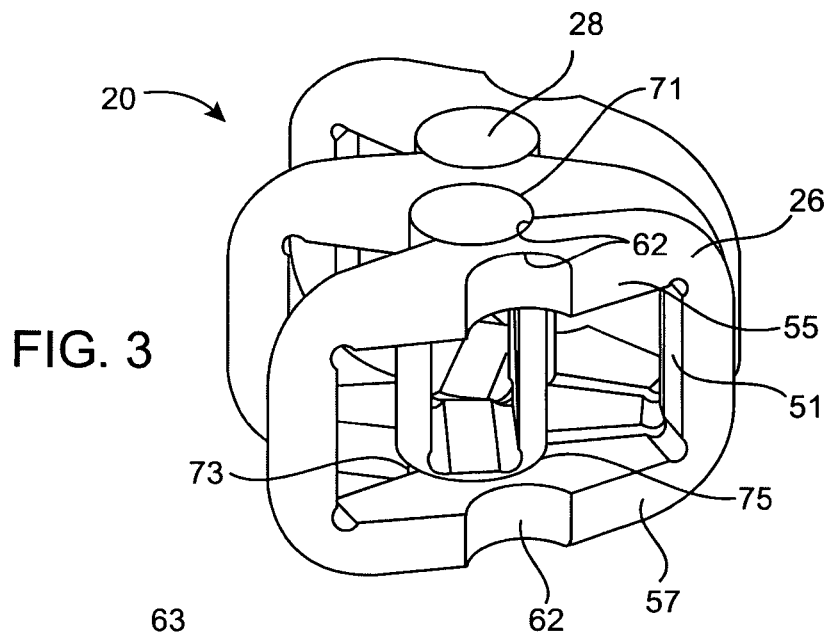
FIG. 3 is a close-up perspective view of a portion of the first preferred embodiment of the articulating shaft.
Figure 4A:
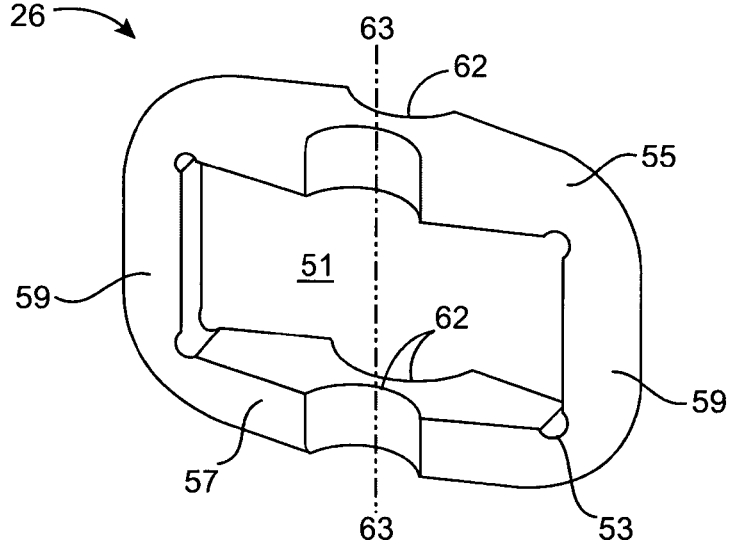
FIG. 4A is a close-up perspective view of a first preferred pivot member of the articulating shaft.
Figure 4B:
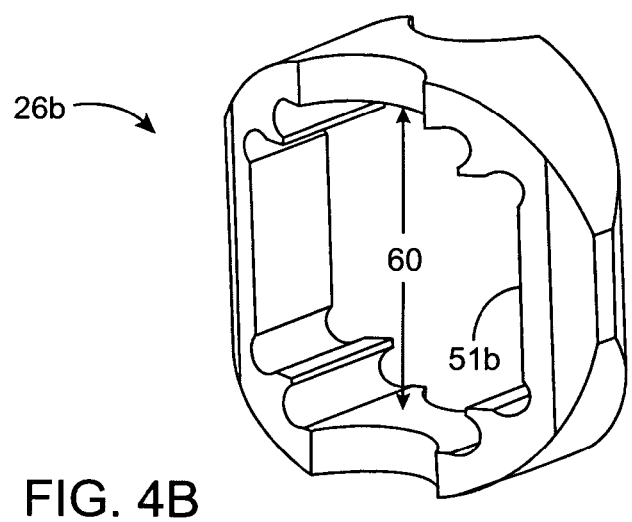
FIG. 4B is a close-up perspective view of a second preferred pivot member of the articulating shaft.

FIG. 3 is a close-up view of a portion of the articulating shaft 20, particularly an alternating combination of pivot members 26 and pins 28 illustrated in a bent configuration. As shown in FIGS. 3 and 4A, each pivot member 26 comprises a single opening, or through hole, 51. The pivot member openings 51 may be formed in a variety of shapes and sizes. In the preferred embodiment, the openings 51 are shaped generally rectangular. Where the openings 51 are rectangular as shown, each pivot member 26 may include rounded, or radiused, corners 53 to minimize stresses in the corners 53 and to provide sufficient clearance for slat assemblies. Each pivot member 26 includes a top portion 55 and a bottom portion 57 joined by side portions 59. The top portion 55 and bottom portion 57 have substantially similar structures. In particular, each of the top portion 55 and bottom portion 57 includes a pair of opposite curved recesses 62 for receiving pins 28, as shown in FIG. 3. The recesses 62 are smoothly curved to facilitate easy pivoting, or rotation, between each pin 28 and an adjacent pivot member 26. To better facilitate a bend in the articulating shaft, each pivot member 26 preferably has a laterally tapered thickness. In particular, the thickness of each pivot member 26 decreases from a medial portion of the pivot member 26 to the lateral, or side, portions 59. Each pivot member 26 defines a vertical axis 63 as shown in FIG. 4.

In FIG. 4A, the opening 51 of the pivot member 26 is shown as generally rectangular. As discussed further below, the articulating shaft 20 may be configured to receive slat assemblies in combination with a variety of other structures with differing sizes, such as an actuator, a tube, electrical wiring, and more. Accordingly, a further preferred pivot member 26b is provided and illustrated in FIG. 4B having a opening 51b with a taller central section 60 for accommodating a larger structure extending therethrough.

In FIGS. 3 and 5, the pin 28 comprises a pin aperture, or through hole, 64 that is also defined by rounded, or radiused, corners 66 to minimize stresses in the corners 66 and to provide sufficient clearance for actuators, conduits or whatever mechanism may be inserted therethrough. As described further below, the pin apertures 64 collectively define an inner passageway, or path, for receiving an actuator, a tube, electrical wiring, or light transmitting media such as optical fibers. Each pin 28 comprises a central portion 68 with an increased diameter than that of the top portion 71 and bottom portion 73 so as to form top and bottom shoulders 75. As shown in FIGS. 3 and 6, the pin shoulders 75 restrict vertical movement between the pin 28 and an adjacent pivot member 26 by abutting the inner surfaces of the top portion 55 and bottom portion 57 of the pivot member 26. Also in FIGS. 3 and 6, the mating of the pin top portion 71 and the pin bottom portion 73 with the curved recesses 62 of the pivot members 26 centers each pin 28 with respect to an adjacent pivot member 26 while enabling free pivoting therebetween. In FIGS. 1 and 6, the openings 51 of the pivot members 26 collectively form an outer passageway through which the slat assemblies 31, 33 are inserted. As shown in FIG. 6, it will be appreciated the preferred embodiment of the device obviates the need for multiple lumens, or bores. By forming the pivot member 26 as a generally rectangular frame with a dominant opening 51, multiple slat assemblies may extend the pivot members 26 without need for aligning any lumens.

In an alternative embodiment shown in FIG. 7, the pin 28b may simply comprise a substantially cylindrical outer surface 77 and a pin aperture 64b.

Figure 8A:
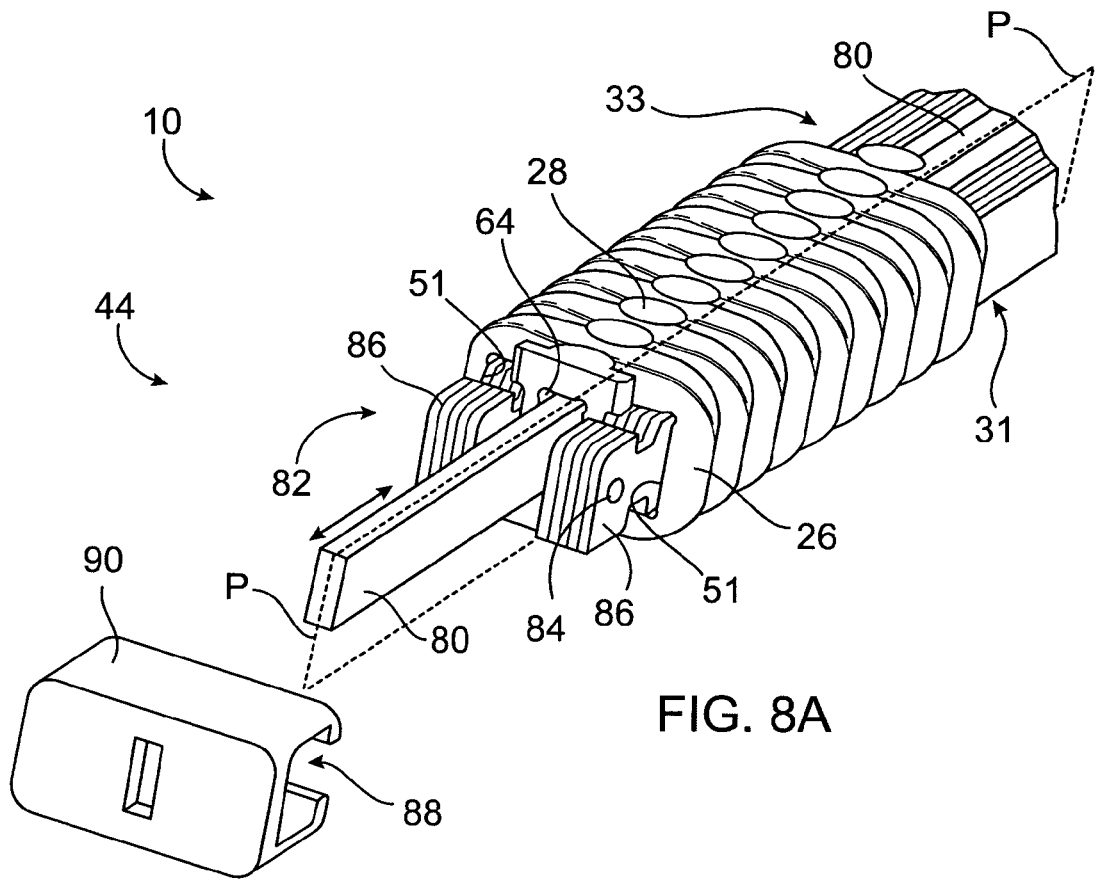
FIG. 8A is a perspective view of a preferred medical device, illustrating the articulating shaft and a rectangular actuator.

FIG. 8A is a perspective view of a partially assembled device 10, shown with slat assemblies 31, 33 and an actuator 80 configured for reciprocating, or oscillating, movement along the axis of the shaft as indicated by the bi-directional arrows. In the illustrated embodiment, the actuator 80 has a rectangular cross-sectional profile with a height greater than its width such that, when it is in a straight configuration, the actuator 80 substantially defines a plane P. Accordingly, the actuator 80 with a rectangular profile thus has a greater elasticity, or flexibility, normal to the plane P than in the plane P. Alternatively stated, the actuator 80 can be easily bent in accordance with the range of motion of the articulating shaft, but not perpendicularly with respect to such range of motion. The actuator 80 is inserted through the pin apertures 64 so as to extend through the articulating shaft 20. The first slat assembly 31 and second slat assembly 33 are inserted through the openings 51 in the pivot members 26. The first slat assembly 31 and second slat assembly 33 extend through the articulating shaft 20 on opposite sides of the pins 28 and the centrally located actuator 80. A connecting mechanism 82 is provided at distal end of each slat assembly 31, 33. In the illustrated embodiment shown in FIG. 8A, the connecting mechanism 82 may comprise transverse slots 84 for receiving bars (not shown). The connecting mechanism 82 may also comprise particularly shaped keys 86 formed at the distal end of the slat assemblies 31, 33 and configured to fit into a slot 88 of a distal tip 90 of the articulating shaft.

Figure 8B:
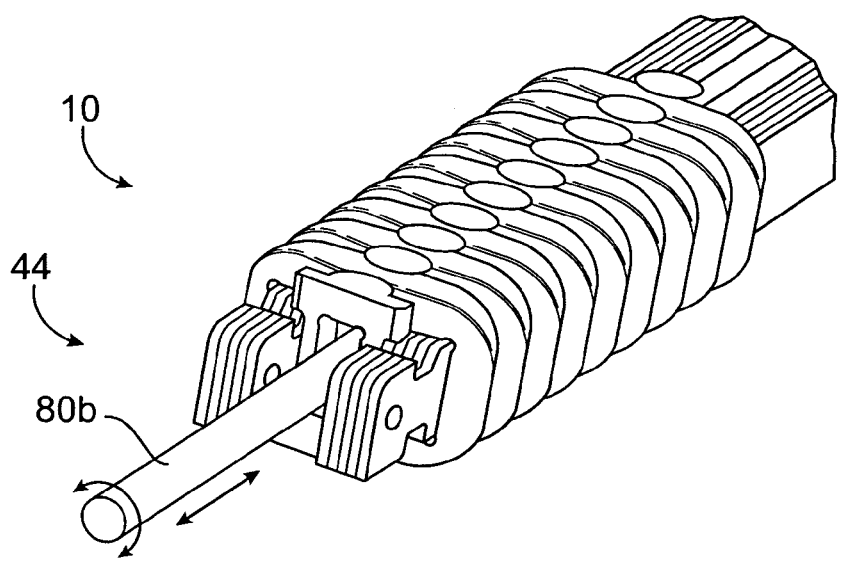
FIG. 8B is a perspective view of a further preferred medical device with a cylindrical actuator.

In FIG. 8B, the device 10 may comprise a cylindrical actuator 80b such that, in addition to a reciprocating motion, it can be rotated to transfer a torsional force from a proximal end of the device 10 to the distal end.

Figure 8C:
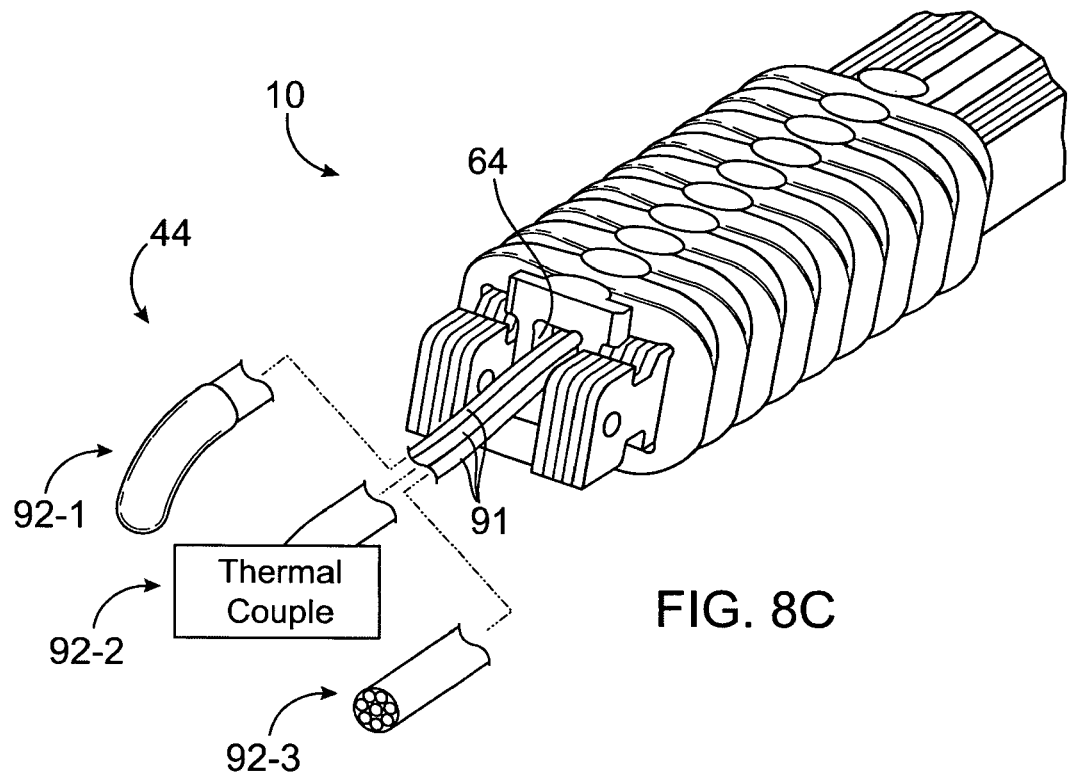
FIG. 8C is a perspective view of further preferred embodiments having electrical wires and/or optical fibers extending through the articulating shaft and a variety of operating mechanisms.

In further embodiments illustrated in FIG. 8C, the device 10 may comprise electrical wiring or optical fibers, both designated by the numeral 91, instead of an actuator extending through the pin apertures 64. The electrical wires or optical fibers 91 may then be coupled to a variety of different operating mechanisms formed at a distal end 44 depending upon the desired application. For example, electrical wiring 91 may be coupled to an electrically activated device, such an RF ablation device 92-1 or an electrically passive device, such as a thermal couple, indicated conceptually by numeral 92-2. As a further example, optical wiring 91 may be provided and coupled to a fiber optic device 92-3, or simply terminated at the distal end 44.

Figure 9:
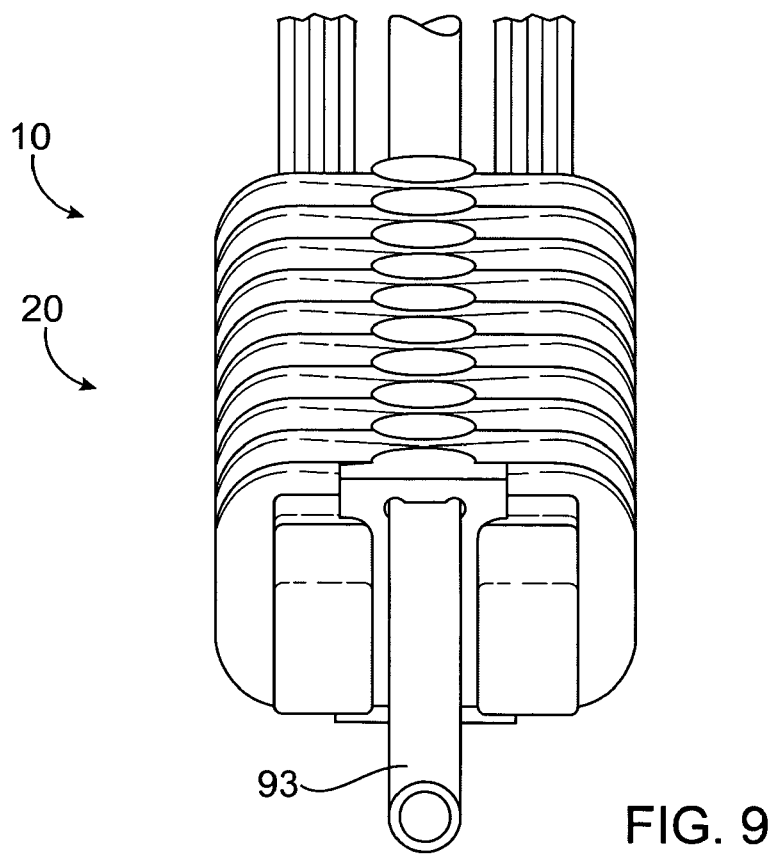
FIG. 9 is perspective view of a further preferred medical device, illustrating the articulating shaft and a tube.

In place of an actuator, the device 10 as shown in FIG. 9 may comprise a tube, or conduit, 93 for providing a pathway or passage for fluids, needles or any other materials of interest that need to be delivered to a desired site. Thus, the articulating shaft 20 according to the invention may be incorporated into a medical device 10 in order to transport or deliver liquids, materials and/or other medical devices to areas within the human body that do not offer a direct pathway.

Figure 10:
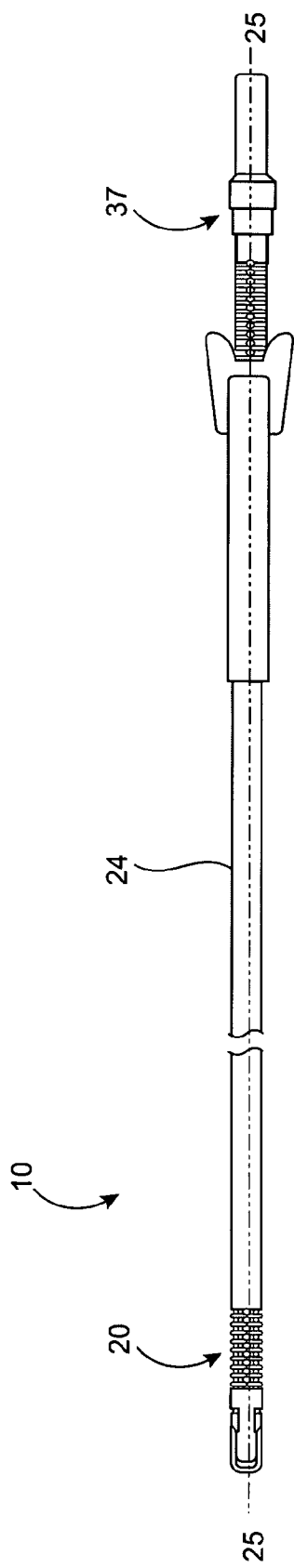
FIG. 10 is a top plan view of the preferred medical device showing the first preferred articulating shaft in a rest state.
Figure 11:
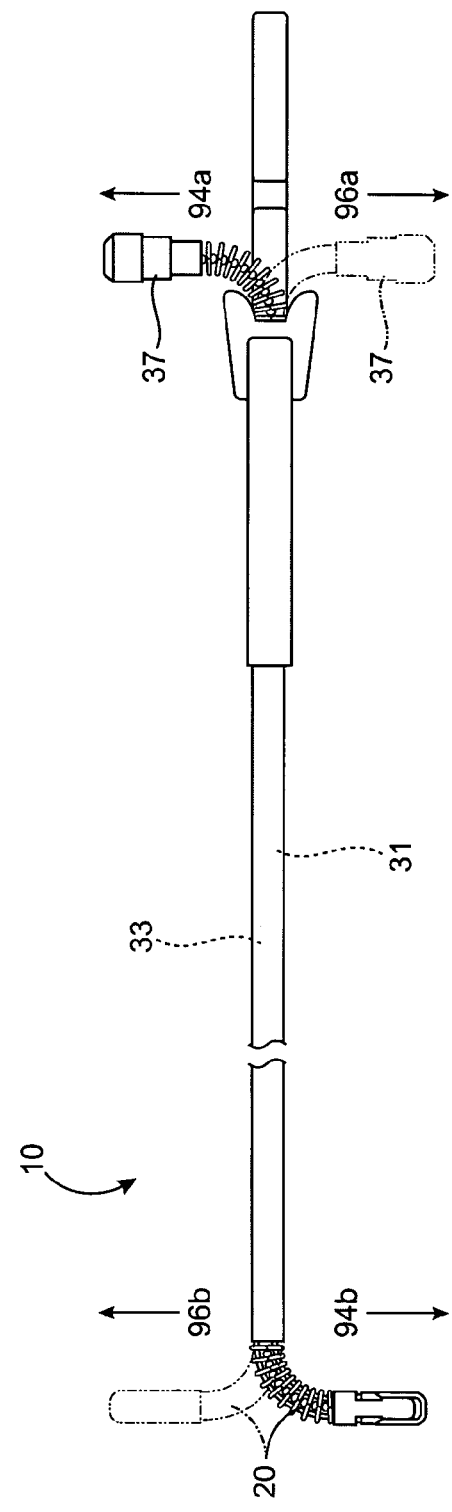
FIG. 11 is a top plan view of the preferred medical device in FIG. 11 showing the articulating shaft bent.

FIGS. 10 and 11 are top operative views of the first preferred embodiment of the device 10. In FIG. 10, the device 10 is shown in a rest, or default, state wherein the articulating shaft 20 and articulator 37 are both straight and, thus, aligned substantially along the axis 25 defined by the rigid proximal shaft portion 24. The articulator 37, and thus the articulating shaft 20, is preferably biased to this straight position, although the device 10 may be formed such that the articulator 37 and articulating shaft 20 are biased to a non-straight, off-axis position.

In FIG. 11, the bending, or articulating, of the articulating shaft 20 is illustrated. In particular, the articulator 37 may be bent in a first direction indicated by arrow 94a, thereby causing the articulating shaft 20 to also bend in an opposite direction 94b. When a user moves the articulator 37 in the first direction 94a, the first slat assembly 31 is pulled, or tensioned, while the second slat assembly 33 is concurrently pushed, or compressed. Unlike certain articulating shafts in the prior art which operate solely by tension, the device 10 according to the invention operates by employing both push and pull forces simultaneously. It will also be appreciated that the dual opposing forces are caused by a single movement of the articulator 37.

In a similar manner, the articulator 37 may be bent in a second direction as shown by phantom lines and indicated by arrow 96a, thereby causing the articulating shaft 20 to also bend in an opposite direction 96b as a result of the first slat assembly 31 being pushed while the second slat assembly 33 is concurrently pulled.

An appreciable advantage of the device 10 is that the articulator 37 is intentionally located for convenient operation by a user. Though it is to be expressly understood that there a variety of ways to move the articulator 37, one appreciable advantage of the device 10 is that the articulator 37 can be moved by the thumb of the same hand holding the handle assembly. Thus, in the preferred embodiment, the articulator 37 is disposed adjacent to and above the handles 48 as shown in FIG. 2. By positioning the articulator 37 in this highly desirable location, it will be appreciated that, where an actuator is employed, the user may both articulate the shaft 20 and actuate the device 10, all with one hand. Though the user may choose to use the other hand to move the articulator 37, it is not required. Instead, the user can simply leave his or her thumb on the articulator 37 at all times to move the articulating shaft 20 to the right or left as desired.

In all embodiments disclosed herein, it will be appreciated that the dual slat assemblies 31, 33 provide sufficient rigidity to the articulating shaft 20. In particular, the dual slat assemblies 31, 33 rigidly maintain the articulating shaft 20 in its straight or bent form without deflection. Though each slat assembly 31, 33 may comprise a single slat, the rigidity of the articulating shaft 20 is enhanced by each slat assembly 31, 33 comprising a plurality of layered slats. Furthermore, by orienting the slats in the vertical direction, the slat assemblies 31, 33 not only rigidly hold the shape of a bent articulating shaft 20, but also prevent any vertical deflection of the articulating shaft 20.

Figure 12:
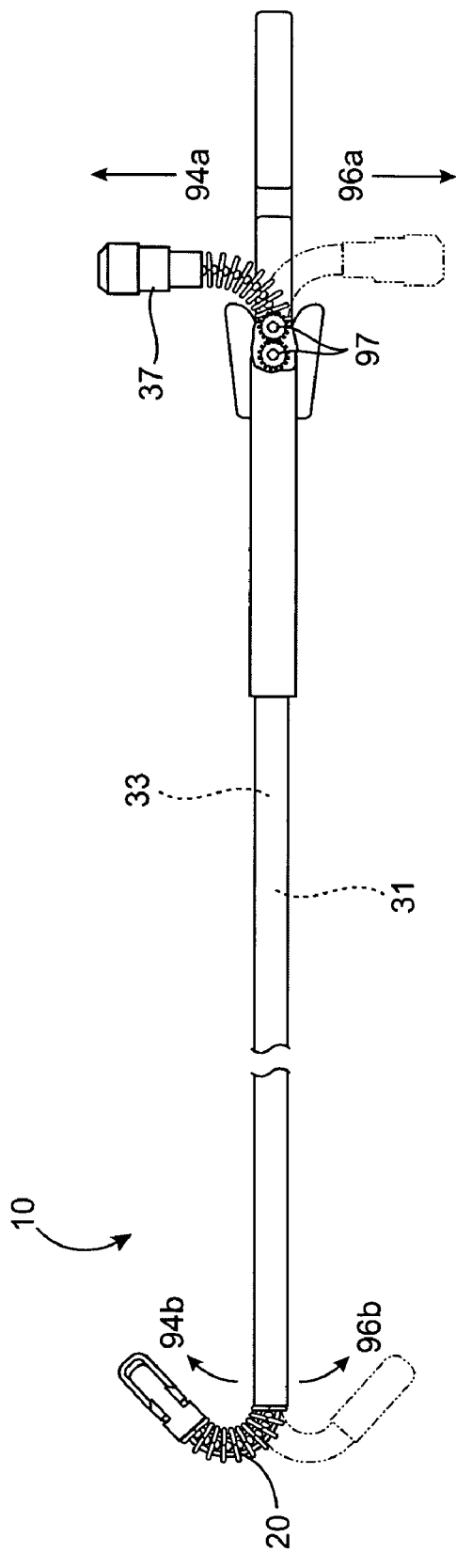
FIG. 12 is a top plan view of an alternative embodiment where the articulating shaft bends in the same direction in which the articulator is moved.

In the preferred embodiment, the articulating shaft 20 is configured to bend in a direction opposite to the manipulated direction of articulator 37. For example, from the vantage point of the user (i.e., looking at the device 10 from the rear), when the articulator 37 is bent to the right, indicated by arrow 94a in FIG. 11, the articulating shaft 20 bends to the left as indicated by arrow 94b in FIG. 11. The device 10 may be configured to reverse the bending motion shown in FIG. 11, such that the articulating shaft 20 bends in the same direction as the articulator 37. Thus, different mechanisms may be employed to reverse the directions of the pushing and pulling forces caused by movement of the articulator 37. In FIG. 12, for example, a set of gears 97 may be provided at the proximal end of the slat assemblies 31, 33 and coupled to the articulator 37. A variety of intermediate links and coupling mechanisms may be employed to couple the slat assemblies 31, 33 to the gears 97. In the embodiment shown in FIG. 12, moving the articulator 37 in a first direction 94a now causes the articulating shaft 20 to bend in the same direction 94b. In particular, moving the articulator to the right 94a will push the first slat assembly 31 and simultaneously pull the second slat assembly 33. Accordingly, moving the articulator 37 in the second direction 96a will cause the articulating shaft 20 to also bend in a similar direction 96b. It should also be appreciated that the articulating shaft 20 may be configured to bend to a greater or lesser degree. In the illustrated embodiment in FIG. 12, the articulating shaft 20 is illustrated with a bend greater than 90° from the axis 25 such that the distal end 44 of the device 10 is now pointing in a proximal direction toward the proximal end 39 of the device 10.

Figure 13:
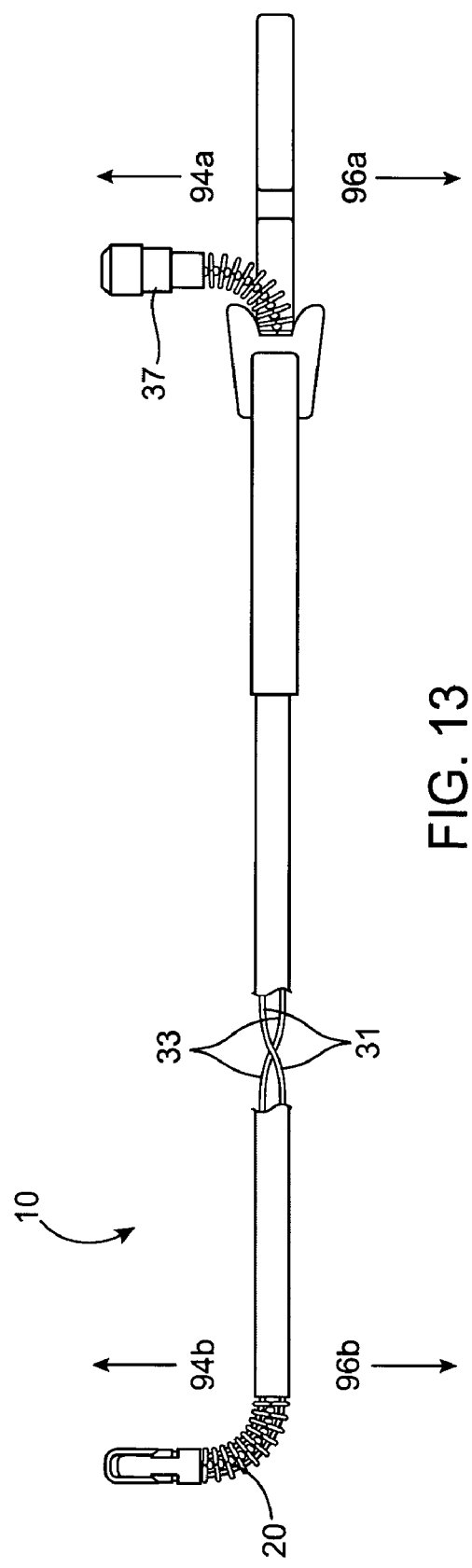
FIG. 13 is a top plan view of a further alternative embodiment where the articulating shaft bends in the same direction in which the articulator is moved.

In a further alternative embodiment shown in FIG. 13, this "same-side" bending may also be accomplished without gears by crisscrossing the slat assemblies 31, 33. Moving the articulator 37 in a first direction 94a pushes the first slat assembly 31 and pulls the second slat assembly 33 such that the articulating shaft 20 also bends in a similar direction 94b as the articulator 37. Accordingly, moving the articulator in the second direction 96a will cause the articulating shaft 20 to also bend in a similar direction 96b. To enable the slat assemblies 31, 33 to criss-cross, the slat assemblies 31, 33 may be disposed on different planes, for example, or provided with slots to enable one assembly to intersect the other. It will be appreciated that a variety of mechanism may be used to accomplish the criss-crossing between the slat assemblies 31, 33.

Figure 14:
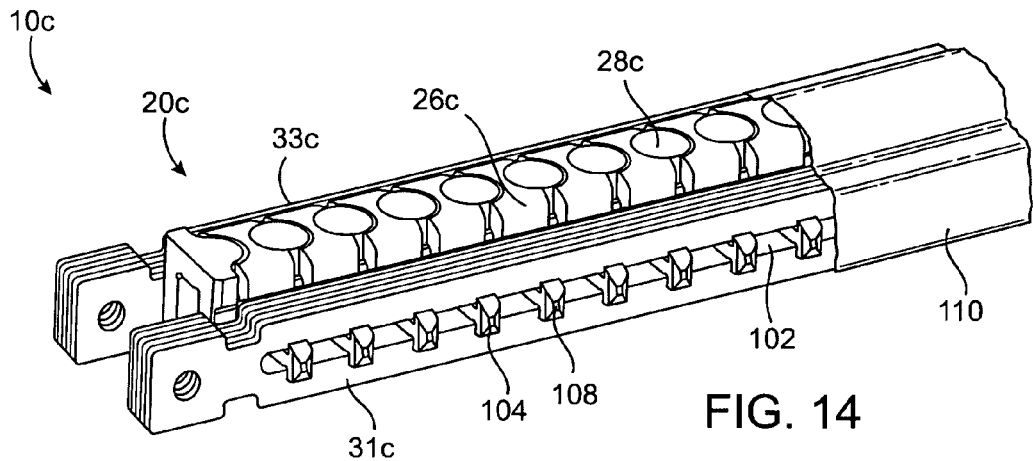
FIG. 14 is a perspective view of an alternate embodiment of an articulating shaft.
Figure 15:
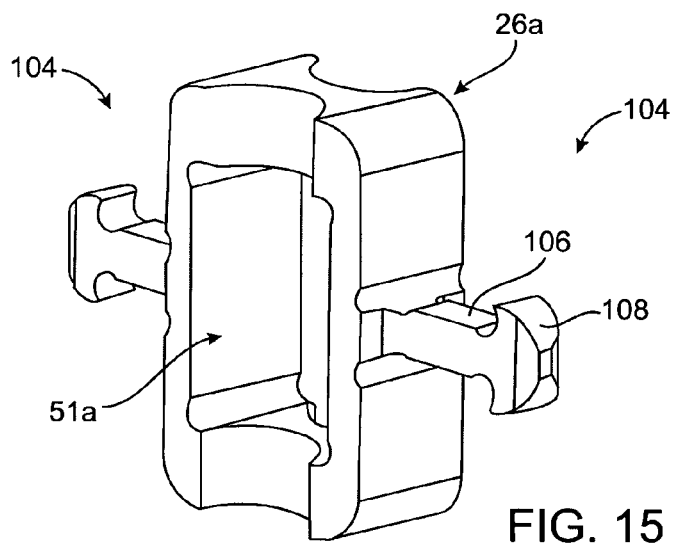
FIG. 15 is a perspective view of an alternate pivot member of the articulating shaft in FIG. 14.

FIG. 14 is a perspective view of an alternative embodiment of a device 10c including an alternative articulating shaft 20c where elements of similar structure are designated by the same reference numerals followed by the lower case "c". In FIG. 14, the device 10c includes a first slat assembly 31c and a second slat assembly 33c, each having an elongate slot 102. The shaft 20c includes a series of alternating pivot members 26c and pins 28c. In FIG. 15, each pivot member 26c includes an opening 51c, and a pair of oppositely extending arms 104. Each arm 104 includes a neck 106 and a lateral tab 108. When assembled, the arms 104 of the pivot members 26c extend laterally through the elongate slots 102 of the slat assemblies 31c, 33c as shown in FIG. 14. The lateral tabs 108 secure the pivot members 26c to the slat assemblies 31c, 33c. The device 10c may also include a sheath 110, shown partially here, over the articulating shaft 20c. It is to be understood that the sheath 110 may be provided in all of the previously disclosed embodiments.

Figure 16:
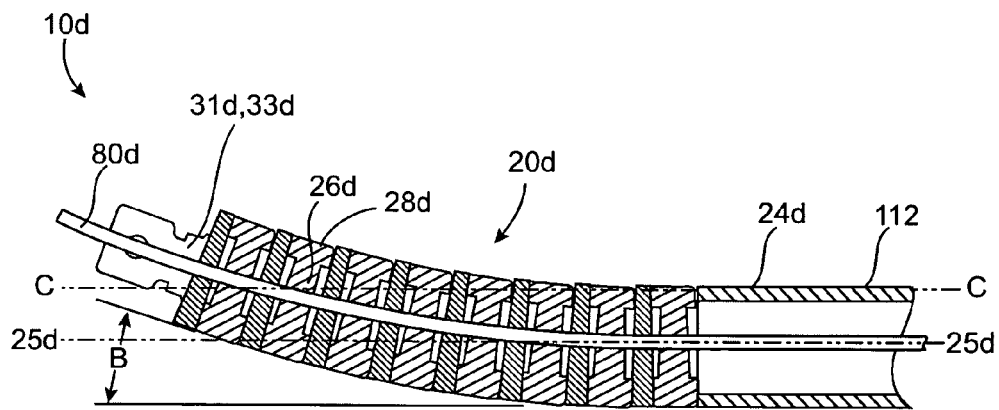
FIG. 16 is a side elevation view of a further alternate embodiment of an articulating shaft.

FIG. 16 is a side elevation view of a further alternative embodiment of a device 10d having a permanent, preconfigured curve. In this embodiment, elements of similar structure are designated by the same reference numerals followed by the lower case "d". In the illustrated embodiment, the articulating shaft 20d is permanently curved to an angle B in a direction that is generally perpendicular to the two-way bending (i.e., range of motion) of the articulating shaft 20d. Alternatively stated, the articulating shaft 20d is preferably configured to bend to the right and left directions, which directions collectively define the range of motion of the articulating shaft 20d. The articulating shaft 20d thus comprises a permanent, preconfigured curve that is perpendicular to this range of motion. The articulating shaft 20d includes pivot members 26d and pins 28d substantially similar in structure to the first preferred embodiment described above in connection with FIGS. 1-11 except that the pivot members 26d and pins 28d may have tapered top portions to better facilitate the permanent upward curve. Here, the permanent curve is in an upward direction while the articulating shaft 20d is bendable to the right and left directions. Accordingly, the slat assemblies 31d, 33d comprise slats formed with permanent curves that conform to the permanent curve of the articulating shaft 20d. The device 10d also includes an actuator 80d that is bent in conformity with the permanent curve of the shaft 20b. It is to be expressly understood that the articulating shaft 20d may be formed with a permanent curve in any direction off the axis 25d of the rigid proximal shaft portion 24d. Accordingly, where a permanent downward curve is formed in the articulating shaft, the pivot members 26d and 28d may be formed with tapered lower portions.

Alternatively described, the device 10d in FIG. 16 includes a rigid shaft portion 24d with a top surface 112 that defines a plane C. The articulating shaft 20d includes a permanent curve that is bent in a direction away from the plane C. Here, the permanent curve of the articulating shaft 20d is shown as being perpendicular to the plane C, namely, upward.

In all of the foregoing embodiments, the articulating shafts may be covered with a flexible sheath.

It will be appreciated that a method is provided for articulating a shaft of a medical device. In FIGS. 1, 10 and 11, the method comprises providing pivot members 26 each having a single opening 51, extending a first slat assembly 31 through the single opening 51 of each pivot member 26, extending a second slat assembly 33 through the single opening 51 of each pivot member 26, pushing one of the first and second slat assemblies 31, 33 while concurrently pulling the other of the first and second slat assemblies 31, 33 to cause the pivot members 26 to collectively form a bend.

The method further comprises providing pins 28 each having a single pin aperture 64, and disposing the pins 28 adjacent to the pivot members 26 in an alternating configuration. The step of pushing one of the first and second slat assemblies 31, 33 while concurrently pulling the other of the first and second slat assemblies 31, 33 comprises moving an articulator 37 with a single finger, preferably a thumb. The step of moving the articulator 37 with the single finger comprises moving the articulator 37 to a left direction to cause the pivot members 26 to collectively form a bend in a first direction, and moving the articulator 37 to the right direction to cause the pivot members 26 to collectively form a bend to in a second direction.

The method further comprises actuating an end operating, or tool, assembly coupled distally to the articulating shaft 20b.

In all of the foregoing embodiments, it will be appreciated that the dual slat assemblies provide sufficient rigidity to the articulating shaft, especially when the articulating shaft is bent.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A medical device, comprising:
   a bendable portion including a plurality of pivot members and pins in an alternating configuration, each pivot member defining an opening, each pin defining a pin aperture;
   a first slat assembly extending through the bendable portion, the first slat assembly comprising a first plurality of layered slats; and
   a second slat assembly extending through the bendable portion, the second slat assembly comprising a second plurality of layered slats;
   wherein each of the first slat assembly and the second slat assembly is configured to push when the other of the first slat assembly and the second slat assembly pulls so as to cause the bendable portion to bend.

2. The device of claim 1, wherein:
   the openings collectively define an outer passageway; and
   the pin apertures collectively define an inner passageway.

3. The device of claim 2, wherein:
   the first slat assembly extends through the outer passageway alongside a first side of the pins; and
   the second slat assembly extends through the outer passageway alongside a second side of the pins opposite the first side of the pins.

4. The device of claim 1, further comprising an actuator extending through the bendable portion.

5. The device of claim 4, further comprising an operating mechanism coupled to the bendable portion, wherein the actuator is configured to actuate the operating mechanism.

6. The device of claim 1, further comprising a flexible tube extending through the bendable portion.

7. The device of claim 6, wherein the flexible tube comprises a passage for delivery of fluids.

8. The device of claim 1, further comprising an articulator coupled to the first slat assembly and the second slat assembly, wherein movement of the articulator causes one of the first and second slat assemblies to push and the other of the first and second slat assemblies to pull simultaneously.

9. The device of claim 8, wherein movement of the articulator in a first direction causes the bendable portion to bend in a second direction away from the first direction.

10. The device of claim 8, wherein movement of the articulator in a first direction causes the bendable portion to bend in a second direction toward the first direction.

11. The device of claim 1, wherein each pivot member defines a vertical axis, the device further comprising means for preventing each pin from moving vertically with respect to an adjacent pivot member.

12. The device of claim 1, wherein each pivot member has a laterally tapered thickness.

13. The device of claim 1, wherein:
the bendable portion is bendable in a first direction and an opposite second direction, the first and second directions collectively defining a range of motion;
the bendable portion comprises a preconfigured curve generally perpendicular to the range of motion.

14. The device of claim 13, wherein the first slat assembly and second slat assembly are curved in conformity with the preconfigured curve.

15. The device of claim 13, further comprising an actuator curved in conformity with the preconfigured curve.

16. The device of claim 13, wherein each pivot member has a tapered top portion.

17. The device of claim 13, wherein each pin has a tapered top portion.

18. The device of claim 1, further comprising an electrical wire extending through the pin apertures.

19. The device of claim 1, further comprising an optical fiber extending through the pin apertures.

20. A medical device, comprising:
a bendable portion including a plurality of pivot members and pins in an alternating configuration and wherein each pivot member comprises a pair of arms extending in opposite directions so as to form a first plurality of arms disposed along a first side of the pivot members and a second plurality of arms disposed along a second opposite side of the pivot members;
a first slat assembly coupled to the bendable portion, the first slat assembly comprising a first slat groove for receiving the first plurality of arms; and
a second slat assembly coupled to the bendable portion, the second slat assembly comprises a second slat groove for receiving the second plurality of arms,
wherein each of the first slat assembly and the second slat assembly is configured to push when the other of the first slat assembly and the second slat assembly pulls so as to cause the bendable portion to bend.

21. A method for articulating a shaft of a medical device, comprising:
providing pivot members each having a single opening;
providing pins each having a single pin aperture;
disposing the pins adjacent to the pivot members in an alternating configuration;
extending a first slat assembly through the single opening of each pivot member;
extending a second slat assembly through the single opening of each pivot member; and
pushing one of the first and second slat assemblies while concurrently pulling the other of the first and second slat assemblies to cause the pivot members to collectively form a bend.

22. The method of claim 21, wherein pushing one of the first and second slat assemblies while concurrently pulling the other of the first and second slat assemblies comprises moving an articulator.

23. The method of claim 22, wherein moving the articulator comprises:
moving the articulator to a left direction to cause the pivot members to collectively form a bend in a first direction; and
moving the articulator to a right direction to cause the pivot members to collectively form a bend in a second direction.

24. The method of claim 21, further comprising actuating an end operating assembly coupled distally to the articulating shaft.

* * * * *